United States Patent [19]

Ishikawa et al.

[11] 4,443,439
[45] Apr. 17, 1984

[54] PESTICIDAL PHENYLTHIONOPHOSPHONIC ACID ESTERS

[75] Inventors: Hiromichi Ishikawa; Kazuhiko Kitaori, both of Atsugi; Satoru Moriyama, Hatano; Tadashi Chono; Tsugio Uchiyama, both of Atsugi, all of Japan

[73] Assignee: Hokko Chemical Industry Co., Ltd., Tokyo, Japan

[21] Appl. No.: 412,004

[22] Filed: Aug. 27, 1982

[30] Foreign Application Priority Data

Sep. 4, 1981 [JP] Japan ................. 56-138322

[51] Int. Cl.³ ............... A01N 57/14; A01N 57/22; C07F 9/40
[52] U.S. Cl. ............................. 424/211; 260/944
[58] Field of Search .................. 260/944; 424/211

[56] References Cited

FOREIGN PATENT DOCUMENTS 50-6724  1/1975  Japan .
52-036628  3/1977  Japan ................. 424/211

Primary Examiner—Anton H. Sutto
Attorney, Agent, or Firm—Larson and Taylor

[57] ABSTRACT

New phenylthionophosphonic acid O,O-di-esters of the general formula:

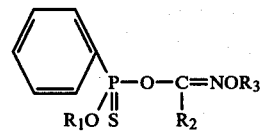

wherein $R_1$ denotes a lower alkyl group; $R_2$ denotes a hydrogen atom, a lower alkyl group or an unsaturated lower alkyl group; and $R_3$ denotes a lower alkyl group or an unsaturated lower alkyl group are provided, which have high insecticidal, miticidal and nematocidal activities and are useful as pesticidal agents to be applied to insect, acarine and/or nematode pests.

8 Claims, No Drawings

PESTICIDAL PHENYLTHIONOPHOSPHONIC ACID ESTERS

BACKGROUND OF THE INVENTION

1. Field of the Invention

This invention relates to new phosphonic acid ester derivatives and, more particularly, to new phenylthionophoshonic acid O,O-di-esters having a high insecticidal activity, high miticidal activity and high nematocidal activity in combination. This invention also relates to a process for the production of these new phosphonic acid ester derivatives, as well as to an insecticidal, miticidal and nematocidal composition containing the above-mentioned new compound as active ingredient.

2. Description of the Prior Art

Many kinds of organo-phosphorus compounds having insecticidal activity, miticidal activity and/or nematocidal activity are known. Thus, O-(N-alkoxy-benzimidoyl)-(thiono)-phosphoric(phosphonic)acid esters having insecticidal and miticidal activities are disclosed in Japanese patent application prepublication "Kokai" No. Sho 47-9149 (corresponding to U.S. Pat. No. 3,760,041), Japanese patent application prepublication "Kokai" No. Sho 49-13335 (corresponding to U.S. Pat. No. 3,872,185) and Japanese patent application prepublications "Kokai" No. Sho 49-132244 and No. Sho 50-64436. O-(N-Alkoxy-substituted alkylimidoyl)-(thiono)phsphoric acid esters are also known to have insecticidal and miticidal activities as disclosed in Japanese patent application prepublications "Kokai" No. Sho 50-6724 and No. Sho 52-33627.

Amongst the insect pests, rice stem borer, brown planthoppers, rice leafhoppers, common cutworms and aphids may be mentioned as the main insect pests which are predominantly infesting aquatic rice plants cultivated in the submerged field or the crops cultivated in upland fields in recent years. For the purpose of combating these main insect pests, there have been applied large quantities of insecticides of the organo-phosphorus compound type, insecticides of the carbamate compound type, insecticides of the chlorinated compound type and others since a long time ago. In these years, there occurs an objectionable phenomena that the main insect pests have gained a resistance against the known insecticidal compounds which have extensively been used in the crop fields.

SUMMARY OF THE INVENTION

An object of this invention is to provide a new insecticide of organophosphorus compound type to which the resistance is not yet gained by the main insect pests of the crop fields. Another object of this invention is to provide a new insecticide of organophosphorus compound type which exhibits a higher insecticidal activity than that of the organophosphorus insecticides conventionally used in the crop fields. Further objects of this invention will be clear from the following descriptions.

We, the present inventors, have synthetized a number of new organophosphonic acid esters and studied their physiological properties. As a result, we have now found that amongst the new organophosphonic acid esters, phenylthionophosphonic acid O,O-di-esters of the general formula:

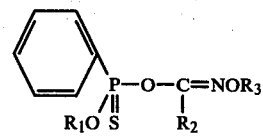

wherein $R_1$ is a lower alkyl group; $R_2$ is a hydrogen atom, a lower alkyl group or an unsaturated lower alkyl group; and $R_3$ is a lower alkyl group or an unsaturated lower alkyl group exhibit a high insecticidal activity, a high miticidal activity and a high nematocidal activity in combination, and that the new compounds of formula (I) show a remarkably high insecticidal activity against the "resistant" strains of insect pests such as green rice leafhopper which have developed the resistance to various kinds of the known organophosphorus type insecticides and of the known carbamate type insecticides.

According to a first aspect of this invention, therefore, there are provided as new compounds phenylthionophosphonic acid O,O-di-esters of the general formula:

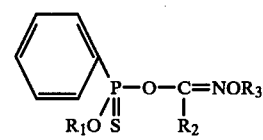

wherein $R_1$ denotes a lower alkyl group; $R_2$ denotes a hydrogen atom, a lower alkyl group or an unsaturated lower alkyl group; and $R_3$ denotes a lower alkyl group or an unsaturated lower alkyl group. The term "an unsaturated lower alkyl group" means inclusively "a lower alkenyl group" and "a lower alkynyl group". The term "lower" means that the concerned group contains 1 to 6 carbon atoms and preferably contains 1 to 4 carbon atoms.

DETAILED DESCRIPTION OF THE INVENTION

According to a specific embodiment of the first aspect of this invention, therefore, there are provided new compounds of the general formula:

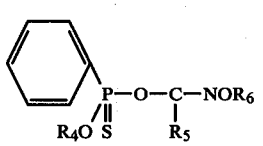

wherein $R_4$ is an alkyl group containing 1–6 carbon atoms, $R_5$ is a hydrogen atom, an alkyl group containing 1–6 carbon atoms, an alkenyl group containing 2–6 carbon atoms or an alkynyl group containing 2–6 carbon atoms, and $R_6$ is an alkyl group containing 1–6 carbon atoms, an alkenyl group containing 2–6 carbon atoms or an alkynyl group containing 2–6 carbon atoms.

More specifically, in formula (I'), $R_4$ is methyl or ethyl group; $R_5$ is hydrogen, methyl, ethyl, n-propyl, i-propyl, n-butyl, vinyl, propenyl or ethynyl group; and $R_6$ is methyl, ethyl, i-propyl, vinyl, allyl or propargyl group.

According to a preferred embodiment of the first aspect invention, there are provided as new compounds phenylthionophosphonic acid O,O-di-esters of the formula:

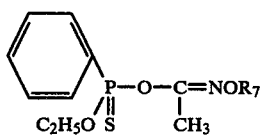

wherein $R_7$ is an alkyl group of 1–4 carbon atoms, an alkenyl group of 2–4 carbon atoms or an alkynyl group of 2–4 carbon atoms.

More specifically, in formula (I''), $R_7$ is methyl, ethyl, i-propyl, allyl or propargyl group.

Although the new compounds of general formula (I), (I') or (I'') according to this invention have a chemical structure similar to that of the known O-(N-alkoxy-benzimidoyl)-(thiono)-phosphoric(phosphonic)acid esters and O-(N-alkoxy-substituted alkylimidoyl)-(thiono)-phosphoric acid esters taught in the chemical literature above-referred to, it has been found that the new compounds of this invention are remarkably superior to the known, similar compounds in the insecticidal activity, miticidal activity and nematocidal activity. Besides, it is observed that the pesticidal activities of the new compounds of this invention are much more rapid and lasting than those of the known, similar compounds and are systemic in nature which makes it possible to achieve the desired pesticidal effect on pests inhabiting on the earth by applying the compounds to aquatic surface or soil. In addition, the new compounds of this invention advantageously exhibit little or no toxicity to mammalian animals and do not exhibit any phyto-toxicity to crop plants at all.

Representative examples of the new compounds of formula (I), (I') or (I'') according to this invention are listed in Table 1 below, together with the structural formulae, boiling point and optical refractive index thereof.

TABLE 1

| Compound No. | Structural formula | Boiling point (°C./mmHg) | Refractive index ($n_D^{24}$) |
|---|---|---|---|
| 1 | $C_6H_5\text{-}P(=S)(OC_2H_5)\text{-}O\text{-}C(H)=NOCH_3$ | 105~108/0.01 | 1.5389 |
| 2 | $C_6H_5\text{-}P(=S)(OC_2H_5)\text{-}O\text{-}C(CH_3)=NOCH_3$ | 103~105/0.01 | 1.5364 |
| 3 | $C_6H_5\text{-}P(=S)(OC_2H_5)\text{-}O\text{-}C(C_2H_5)=NOCH_3$ | 104~107/0.01 | 1.5328 |
| 4 | $C_6H_5\text{-}P(=S)(OC_2H_5)\text{-}O\text{-}C(C_3H_7(n))=NOCH_3$ | 110~112/0.01 | 1.5291 |
| 5 | $C_6H_5\text{-}P(=S)(OC_2H_5)\text{-}O\text{-}C(C_3H_7(i))=NOC_2H_5$ | 109~112/0.01 | 1.5288 |
| 6 | $C_6H_5\text{-}P(=S)(OC_2H_5)\text{-}O\text{-}C(C_4H_9(n))=NOCH_3$ | 113~115/0.01 | 1.5280 |
| 7 | $C_6H_5\text{-}P(=S)(OC_2H_5)\text{-}O\text{-}C(CH=CH_2)=NOCH_3$ | 110~114/0.015 | 1.5409 |
| 8 | $C_6H_5\text{-}P(=S)(OC_2H_5)\text{-}O\text{-}C(CH=CHCH_3)=NOCH_3$ | 112~116/0.015 | 1.5393 |

TABLE 1-continued

| Compound No. | Structural formula | Boiling point (°C./mmHg) | Refractive index ($n_D^{24}$) |
|---|---|---|---|
| 9 | 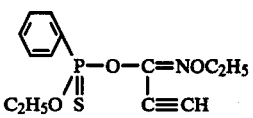 | 107~110/0.015 | 1.5492 |
| 10 | 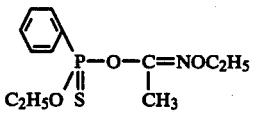 | 105~108/0.01 | 1.5333 |
| 11 | 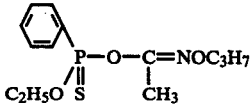 | 108~111/0.01 | 1.5276 |
| 12 | 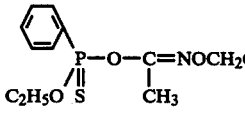 | 112~115/0.015 | 1.5411 |
| 13 | 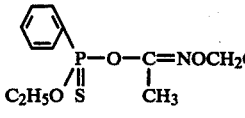 | 106~109/0.015 | 1.5497 |
| 14 | 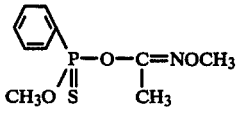 | 98~102/0.007 | 1.5394 |
| 15 | 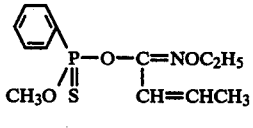 | 97~100/0.007 | 1.5490 |
| 16 | 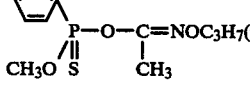 | 101~104/0.007 | 1.5302 |
| 17 | 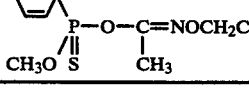 | 98~102/0.007 | 1.5479 |

Chemical designations of Compounds Nos. 1 to 17 given in Table 1 above are as follows:
(1) O-ethyl,O-(N-methoxyformimidoyl)phenylthionophosphonate (Compound No. 1);
(2) O-ethyl,O-(N-methoxyacetimidoyl)phenylthionophosphonate (Compound No. 2);
(3) O-ethyl,O-(N-methoxypropionimidoyl)phenylthionophosphonate (Compound No. 3);
(4) O-ethyl,O-(N-methoxy-n-butyrimidoyl)phenylthionophosphonate (Compound No. 4);
(5) O-ethyl,O-(N-ethoxy-i-butyrimidoyl)phenylthionophosphonate (Compound No. 5);
(6) O-ethyl,O-(N-methoxyvalerimidoyl)phenylthionophosphonate (Compound No. 6);
(7) O-ethyl,O-(N-methoxyacrylimidoyl)phenylthionophosphonate (Compound No. 7);
(8) O-ethyl,O-(N-methoxycrotonimidoyl)phenylthionophosphonate (Compound No. 8);
(9) O-ethyl,O-(N-ethoxypropionimidoyl)phenylthionophosphonate (Compound No. 9);
(10) O-ethyl,O-(N-ethoxyacetimidoyl)phenylthionophosphonate (Compound No. 10);
(11) O-ethyl,O-(N-i-propoxyacetimidoyl)phenylthionophosphonate (Compound No. 11);
(12) O-ethyl,O-(N-allyloxyacetimidoyl)phenylthionophosphonate (Compound No. 12);
(13) O-ethyl,O-(N-propargyloxyacetimidoyl)phenylthionophosphonate (Compound No. 13);

(14) O-methyl,O-(N-methoxyacetimidoyl)phenylthionophosphonate (Compound No. 14);
(15) O-methyl,O-(N-ethoxycrotonimidoyl)phenylthionophosphonate (Compound No. 15);
(16) O-methyl,O-(N-i-propoxyacetimidoyl)phenylthionophosphonate (Compound No. 16); and
(17) O-methyl,O-(N-allyloxyacetimidoyl)phenylthionophosphonate (Compound No. 17).

The new compounds of general formula (I), (I') or (I") according to this invention can be produced by a process which is shown by the following reaction equation:

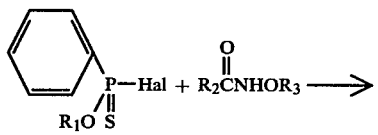

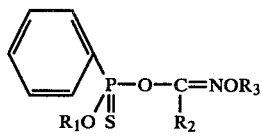

in which $R_1$, $R_2$ and $R_3$ have the same meanings as defined above and Hal denotes a halogen atom such as chlorine or bromine.

According to a second aspect of this invention, therefore, there is provided a process for the production of a phenylthionophosphonic acid O,O-di-ester of the general formula:

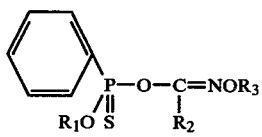

wherein $R_1$ denotes a lower alkyl group; $R_2$ denotes a hydrogen atom, a lower alkyl group or an unsaturated lower alkyl group; and $R_3$ denotes a lower alkyl group or an unsaturated lower alkyl group, which comprises reacting a phenylthionophosphonic halide of the general formula:

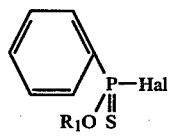

wherein Hal denotes a halogen atom and $R_1$ has the same meaning as defined above with a hydroxamate of the general formula:

wherein $R_2$ and $R_3$ have the same meanings as defined above.

In the process of this invention, the reaction may be conducted in the presence of a base acting as an acid-binding agent, if required. The base available for this purpose includes inorganic bases, for example, an alkali metal hydroxide such as sodium hydroxide or potassium hydroxide; an alkali metal carbonate such as sodium carbonate or potassium carbonate; an alkali metal alcoholate such as sodium methoxide; sodium hydride; metallic sodium; as well as organic bases, for example, a tertiary amine such as triethylamine, dimethylaniline, pyridine and the like which have been employed conventionally as the acid-binding agents. The reaction is conducted preferably in an inert organic solvent which may be, for example, aliphatic or aromatic hydrocarbons such as benzene, toluene, xylene, and petroleum benzine; chlorinated aliphatic or aromatic hydrocarbons such as carbon tetrachloride, methylene chloride, chloroform and chlorobenzene; ketones such as acetone, methyl ethyl ketone, methyl isopropyl ketone and methyl isobutyl ketone; ethers such as diethylether, dibutylether, tetrahydrofuran and dioxane; and nitriles such as acetonitrile and propionitrile.

The reaction temperature may vary within a wide range and usually be in a range of 0° C. to 120° C. and preferably in a range of 20° C. to 80° C. The reaction may proceed under atmospheric pressure, though the reaction may be conducted under an elevated pressure, if desired. The reactants of the formulae (II) and (III) may preferably be present in a substantially equimolar proportion in the reaction mixture.

The new compounds of this invention are effective to combat a wide variety of insect pests such as insects sucking as the bait the body juice of plants or animals; and insects chewing a portion of plants or animals or a material of vegetable or animal origin, as well as acarine pests and nematodes. The insect and acarine pests which may be combatted with the new compounds of this invention include those associated with agriculture (including the growing of crops for food and fibre, horticulture and animal husbandry), such as the insect and acarine pests infesting the growing plants, those associated with forestry, the storage of products of vegetable origin, such as grains, fruits and timber, and also the pests associated with the transmission of diseases of man and animals, such as houseflies and mosquitos. The new compounds of this invention are useful to combat a wide variety of the insect and acarine pests as mentioned below.

Thus, the pests which may be combatted with the new compounds of this invention include: Coleoptera insect pests such as azuki bean weevil (*Callosobruchus chinensis*), maize weevil (*Sitophilus zeamais*), red flour beetle (*Tribolium castaneum*), twenty-eight-spotted ladybird (*Henosepilachna vigintioctopunctata*) and barley wireworm (*Agriotes fuscicollis*); Lepidopterous insect pests such as gypsy moth (*Lymantria dispar*), common cabbageworm (*Pieris rapae*), common cutworm (*Spodoptera litura*), rice stem borer (*Chilo suppressalis*), summer fruit tortrix (*Adoxophyes orana fasciata*) and almond moth (*Ephestia cautella*); Hemipterous insect pests such as green rice leafhopper (*Nephotettix cincticeps*), brown rice planthopper (*Nilaparvata lugens*), small rice planthopper (*Laodelphax striattellus*), comstock mealybug (*Pseudococcus comstocki*), green peach aphid (*Myzus persicae*), and apple aphid (*Aphis pomonella*); Orthopterous insect pests such as German cockroach (*Blattella germanica*), American cockroach (*Periplaneta americana*), and African mole cricket (*Gryllotalpa africana*); Dipterous insect pests such as house fly (*Musca domes-*

*tica*), yellow-fever mosquito (*Aedes aegypti*), seedcorn maggot (*Hylemya platura*) and smaller house mosquiot (*Culex tritaeniorhynchus*); and Thripidae insect pests such as southern yellow thrips (*Thrips palmi*). The acarine pests which may be combatted with the new compounds of this invention include: carmine spider mite (*Tetranychus cinnabarinus*), two-spotted spider mite (*Tetranychus urticae*), citrus red mite (*Panonychus citri*) and pink citrus rust mite (*Aculops pelekassi*) and the like. The nematodes which may be combatted with the new compounds of this invention include: southern root-knot nematode (*Meloidogyne incognita*), rice white-tip nematode (*Aphelenchoides besseyi*), soybean cyst nematode (*Heterodera glycines*) and others.

In use, the new compounds of this invention may be applied to the pests, to the locus of the pests, to the habitat of the pests, or to growing plants liable to infestation by the pests, by any of the known means of applying the pesticidal compounds, for example, by dusting or spraying. The new compounds of this invention may be formulated into conventional formulations or preparations for pesticidal usage, by mixing the active compound of this invention with an acceptable known diluent or carrier material.

According to a third aspect of this invention, therefore, there is provided an insecticidal, miticidal and nematocidal composition comprising an insecticially, miticidally and/or nematocidally effective amount of a phenylthionophosphonic acid O,O-di-ester of the general formula:

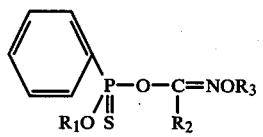

wherein $R_1$ denotes a lower alkyl group; $R_2$ denotes a hydrogen atom, a lower alkyl group or an unsaturated lower alkyl group; and $R_3$ denotes a lower alkyl group or an unsaturated lower alkyl group, as the active ingredient, in combination with an acceptable diluent or carrier. The compounds of formula (I) which are used in the composition of this invention may preferably be the new compounds of general formula (I') or (I'') given above.

The pesticidal (insecticidal, miticidal and nematocidal) composition of this invention may be prepared by formulating a new compound of general formula (I) into the form of emulsifiable concentrate, wettable powder, flowable powder, dusting powder, driftless (DL-type) powder, granules, fine granules, tablets, liquid preparations, etc., according to conventional formulation techniques. The carrier materials to be used may be solid or liquid ones which have been used conventionally in the preparations for agricultural and horticultural usages. The available carriers in the composition of this invention are not limited to any particular one. The solid carriers available include, for example mineral powders such as kaolin, bentonite, clay, montmorillonite, talc, diatomaceous earth, mica, vermiculite, gypsum, calcium carbonate, apatite, kieselguhr, white carbon, slaked lime, siliceous sand, ammonium sulfate and urea; vegetable materials such as soybean powder, wheat flour, wood meal, tobacco powder, starch and crystalline cellulose; polymeric compounds such as petroleum resin, polyvinyl chloride, ketone resin and dammar gum; alumina, silicates, polysaccharide, colloidal silica and waxes. The liquid carriers available include, for example, water; alcohols such as methanol, ethanol, n-propanol, isopropanol, butanol, ethylene glycol and benzyl alcohol; aromatic hydrocarbons such as benzene, toluene, xylene, ethylbenzene and methylnaphthalene; halogenated hydrocarbons such as chloroform, carbon tetrachloride, dichloromethane, chloroethylene, monochlorobenzene, trichlorofluoromethane and dichlorodifluoromethane; ethers such as ethylether, ethylene oxide, dioxane and tetrahydrofuran; ketones such as acetone, methyl ethyl ketone, cyclohexanone, methyl isobutyl ketone and isophorone; esters such as ethyl acetate, butyl acetate, ethylene glycol acetate and amyl acetate; acid amides such as dimethylformamide and dimethylacetamide; nitriles such as acetonitrile, propionitrile and acrylonitrile; sulfoxides such as dimethylsulfoxide; alcoholethers such as ethylene glycol monomethylether and ethylene glycol monoethylether; aliphatic and cycloaliphatic hydrocarbons such as n-hexane, cyclohexane, industrial gasoline (petroleum ether, solvent naphtha, etc.) and petroleum fractions (paraffins, kerosene, gas oil, etc.).

When the active compound of this invention is formulated in the form of an emulsifiable concentrate, wettable powder, flowable sols, etc., one or more surface active agents are used for the purposes of emulsification, dispersion, solubilization, wetting, foaming, lubrication and/or spreading. Surface active agents may be of nonionic, anionic, cationic and amphoteric types. Examples of the nonionic type are polyoxyethylene alkylethers, polyoxyethylene alkylesters, polyoxyethylene sorbitanalkylesters, sorbitan alkylesters and the like. Examples of the anionic type are alkylbenzene sulfonates, alkylsulfosuccinates, alkyl sulfates, polyoxyethylene alkylsulfates, aryl sulfonates and the like. Examples of the cationic type include quaternary ammonium compounds such as stearyl trimethyl ammonium chloride and alkyl dimethylbenzyl ammonium chloride and polyoxyethylene alkylamines. Examples of the amphoteric type are carboxylic acids of betaine type and alkyl sulfates.

Other additives which may be used as an adjuvant include polyvinyl alcohol, carboxymethylcellulose, acasia gum, polyvinyl acetate, gelatin, casein, sodium alginate and tragacanth gum, for example.

The composition according to this invention in the form of a variety of formulations as above-mentioned may contain 0.1 to 95%, preferably 0.5 to 90%, by weight, of a phenylthionophosphonic acid O-alkyl,O-(N-alkoxyalkanoylimidoyl)ester of formula (I) according to this invention. Thus, the composition may usually contain 0.1 to 5% by weight of the active compound when formulated in the form of dusting powder, DL powder or fine granules, 1 to 10% by weight in the form of granules and 5 to 95% by weight in the form of wettable powder, emulsifiable concentrate or liquid preparations.

When the composition of this invention is in the form of dusting powder, DL powder, fine granules or granules, the composition will be applied as such to plants, surfaces and/or interior of soils or aquatic fields upon or in which pests, mites and/or nematodes are living at a rate of 2 to 5 kg per 10 ares (or at a rate of 50 to 500 g of the active ingredient per 10 ares). For nematocidal purposes, in particular, the composition may be applied even at a higher rate of about 500 to 10,000 g of the active ingredient per 10 ares. The composition in the form of emulsifiable concentrate, wettable powder, liquid preparations or flowable sols may usually be diluted with water or a suitable solvent before use to give a concentration of the active ingredient of about 5 to 1,000 ppm, preferably about 50 to 500 ppm, the dilute formulation being usually applied at a rate of 100 to 300 l per 10 ares. Emulsifiable concentrate, liquid preparations and flowable sols may also be applied as such or in a diluted form with a small amount of water, i.e. in the form of a LV spray or ULV spray, at a rate of about 50 to 3000 ml per 10 ares mainly as aerial spraying agent.

The composition of this invention may further incorporate, if desired, other insecticide, miticide, nematocide, fungicide and/or herbicide.

According to a further aspect of this invention, there is provided a method of combating insect pests, acarine pests and/or nematode pests at a locus of infestation, which comprises treating the pests or the locus of infestation with an insecticidally, miticidally or nematocidally effective amount of a compound of general formula (I), (I') or (I'').

The invention is now illustrated with reference to the following Examples. Examples 1 to 3 are illustrative of the production of the new compounds of this invention; Examples 4 to 7 illustrative of the formulations comprising the new compound of this invention; and Examples 8 to 18 are illustrative of the pesticidal properties of the new compounds of this invention.

EXAMPLE 1

Production of Compound No. 2 of the formula:

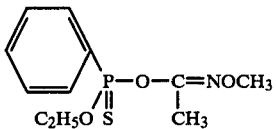

To a solution of methyl acetohydroxamate (8.9 g) in methyl ethyl ketone (100 ml) was added potassium hydroxide (5.6 g) and the mixture was heated at 50° C. for 1 hour under stirring. Then, O-ethyl-phenylthionophosphonic chloride (22.1 g) was added to the reaction mixture and the reaction was conducted at 80° C. for 5 hours under stirring. After the methyl ethyl ketone was distilled off under a reduced pressure, benzene (200 ml) was added to the residue and the resulting solution was washed with water (200 ml), then with a 2% aqueous sodium hydroxide solution and finally with water until the washings became neutral. The solution thus washed was dried over anhydrous sodium sulfate, subjected to a distillation under a reduced pressure to remove the benzene therefrom and then to a vacuum distillation to yield O-ethyl, O-(N-methoxyacetimidoyl) phenylthionophosphonate (19.7 g; 72%).

b.p. 103°–105° C./0.01 mmHg; $n_D^{24}$ 1.5364.

EXAMPLE 2

Production of Compound No. 12 of the formula:

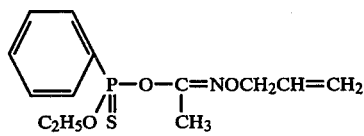

To a solution of allyl acetohydroxamate (11.5 g) in acetonitrile (100 ml) was added potassium hydroxide (5.6 g) and the mixture was heated at 50° C. for 1 hour under stirring. Then, O-ethyl-phenylthionophosphonic chloride (22.1 g) was added to the mixture and the reaction was conducted at 80° C. for 5 hours under stirring. After the acetonitrile was distilled off under a reduced pressure, benzene (200 ml) was added to the residue and the resulting solution was washed with water (200 ml), then with a 2% aqueous sodium hydroxide solution and finally with water until the washings became neutral. The solution thus washed was dried over anhydrous sodium sulfate, subjected to a distillation under a reduced pressure to remove the benzene therefrom and then to a vacuum distillation to yield O-ethyl, O-(N-allyloxyacetimidoyl) phenylthionophosphonate (16.2 g; 54%).

b.p. 112°–115° C./0.015 mmHg; $n_D^{24}$ 1.5411

EXAMPLE 3

Production of Compound No. 1 of the formula:

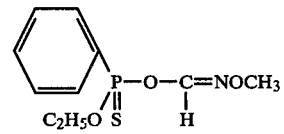

To a solution of methyl formhydroxamate (7.5 g) in tetrahydrofuran (100 ml) was added sodium hydride (4.0 g as 60% suspension in oil) under ice-cooling and the mixture was stirred at room temperature for 10 minutes. Then, O-ethyl-phenylthionophosphonic chloride (22.1 g) was added to the mixture and the reaction was conducted at 65° C. for 2 hours under stirring. The reaction solution, after the addition of benzene (200 ml) thereto, was washed with water (200 ml), then with a 2% aqueous sodium hydroxide solution and finally with water until the washings became neutral. The solution thus washed was dried over anhydrous sodium sulfate, subjected to a distillation under a reduced pressure to remove the solvent used and then to a vacuum distillation to yield O-ethyl, O-(N-methoxyformimidoyl) phenylthionophosphonate (19.2 g; 74%).

b.p. 105°–108° C./0.01 mmHg; $n_D^{24}$ 1.5389.

EXAMPLE 4

Emulsifiable concentrate

40 Parts (by weight) of the Compound No. 2 prepared in the Example 1, 20 parts (by weight) of an emulsifying agent consisting of the condensation product of ethylene oxide with fatty alcohols (available as a tradename "Solpol 700H", a product of Toho Chemical Industry Company, Japan), and 40 parts (by weight) of xylene were mixed together uniformly to give an emulsifiable concentrate which may be diluted with water upon use to give a sprayable emulsion.

EXAMPLE 5

Wettable powder

25 Parts (by weight) of the Compound No. 11 listed in Table 1, 15 parts (by weight) of white carbon (finely divided silica), 3 parts (by weight) of calcium ligninesulfonate, 2 parts (by weight) of a polyoxyethylene-nonylphenylether as the non-ionic emulsifier, 5 parts (by weight) of diatomaceous earth and 50 parts (by weight) of clay were ground together and mixed uniformly with each other in a mixer to give a wettable powder which may be dispersed in water upon use.

EXAMPLE 6

Dusting powder 1.5 Parts (by weight) of the Compound No. 14 listed in Table 1 was mixed well with 98.5 parts (by weight) of clay, followed by grinding to small particle size. A dusting powder was obtained, which was directly be applied by a known dusting device.

EXAMPLE 7

Granules

5 Parts (by weight) of the Compound No. 2, 1.5 parts (by weight) of lauryl sulfate, 1.5 parts of calcium ligninesulfonate and 67 parts of kaolin were admixed with 15 parts (by weight) of water, followed by kneading in a kneader and granulation in a granulator. The granules so shaped were then dried in a fluidizing drier to give granules which may directly be applied to the soil.

EXAMPLE 8

This Example illustrates the test of estimating the insecticidal activity of test compounds against rice stem borer.

Aquatic rice plants of average height of about 50 cm which had been grown in a pot having an area of 1/10,000 ares at the soil surface were infested with 30 larvae of rice stem borer (*Chilo suppressalis*) which had just hatched from the eggs. 5 Days after the infestation, the rice plants and the larvae were sprayed with the composition under test which was prepared by diluting with water the wettable powder of this invention made according to the preceding Example 5 to the concentration of the active compound as indicated in Table 2 below. The composition was sprayed by means of a spraygun and was applied at the rate of application of 50 ml per three pots. 5 Days after the spraying, the rice plants were dissected and the numbers of the dead larvae and the surviving larvae were counted, respectively, and percent of mortality was assessed. The tests were conducted with three replicates for a particular value of the concentration of the active compound under test, and the average of % mortality was calculated. The results (expressed as averaged % mortality) are set out in Table 2 below.

TABLE 2

| Test Compounds | Mortality (%) Concentration of active Compound sprayed (ppm) | |
|---|---|---|
| | 100 | 50 |
| Compound No. 1 | 100 | 95 |
| Compound No. 2 | 100 | 100 |
| Compound No. 3 | 100 | 95 |
| Compound No. 4 | 100 | 93 |
| Compound No. 5 | 100 | 93 |
| Compound No. 6 | 100 | 93 |
| Compound No. 7 | 100 | 95 |
| Compound No. 8 | 100 | 95 |
| Compound No. 9 | 100 | 93 |
| Compound No. 10 | 100 | 95 |
| Compound No. 11 | 100 | 100 |
| Compound No. 12 | 100 | 100 |
| Compound No. 13 | 100 | 93 |
| Compound No. 14 | 100 | 95 |
| Compound No. 15 | 100 | 95 |
| Compound No. 16 | 100 | 95 |
| Compound No. 17 | 100 | 95 |
| Comparative Compound A | 78 | 47 |
| Comparative Compound B | 60 | 35 |

TABLE 2-continued

| Test Compounds | Mortality (%) Concentration of active Compound sprayed (ppm) | |
|---|---|---|
| | 100 | 50 |
| Comparative Compound C | 73 | 55 |
| Comparative Compound D | 78 | 47 |
| Comparative Compound E | 80 | 60 |
| Comparative Compound F | 80 | 57 |
| Comparative Compound G | 100 | 67 |
| Comparative Compound H | 80 | 57 |
| No treatment (Control) | 0 | |

Compound Nos. 1 to 17 as above are identical to those listed in Table 1 before. The same reference is made in the following tables in this specification.

Comparative compound A: $(C_2H_5O)_2\underset{\underset{S}{\|}}{P}-O-C(=NOC_2H_5)(C_6H_5)$ (see U.S. Pat. No. 3,760,041)

Comparative compound B: $(C_2H_5)(C_2H_5O)\underset{\underset{S}{\|}}{P}-O-C(=NOC_2H_5)(2\text{-}Cl\text{-}C_6H_4)$ (see U.S. Pat. No. 3,760,041)

Comparative compound C: $(C_2H_5O)_2\underset{\underset{S}{\|}}{P}-O-C(=NOC_2H_5)(4\text{-}OCH_3\text{-}C_6H_4)$ (see U.S. Pat. No. 3,872,185)

Comparative compound D: $(C_2H_5O)_2\underset{\underset{S}{\|}}{P}-O-C(=NOC_2H_5)(2\text{-}SCH_3\text{-}C_6H_4)$ (see U.S. Pat. No. 3,872,185)

Comparative compound E: $(C_2H_5O)_2\underset{\underset{S}{\|}}{P}-O-C(=NOC_2H_5)(4\text{-}CN\text{-}C_6H_4)$ (see Japanese patent application prepublication "Kokai" Sho 49-132244)

Comparative compound F: $(C_2H_5O)_2\underset{\underset{S}{\|}}{P}-O-C(=NOCH_3)(2,4\text{-}Cl_2\text{-}C_6H_3)$ (see Japanese patent application prepublication "Kokai" Sho 50-64436)

Comparative compound G: $(C_2H_5O)_2\underset{}{P}-C(=NOCH_3)(CH_2SCH_3)$ (see Japanese patent application -continued

| | |
|---|---|
| | prepublication "Kokai" Sho 50-6724) |
| Comparative compound H: | $(C_2H_5O)_2\underset{\underset{S}{\|}}{P}-O-\underset{\underset{CH_2Cl}{\|}}{C}=NOC_2H_5$ (see Japanese patent application prepublication "Kokai" Sho 52-33627) |

EXAMPLE 9

This Example illustrates the test of estimating the insecticidal activity of test compounds against red flour beetle.

A sheet of filter paper placed on the bottom of a glass Petri dish of 9 cm diameter was sprayed with 1 ml of the composition under test which was prepared by diluting with water the emulsifiable concentrate of this invention made in the Example 4, to the concentration of the active compound indicated in Table 3 below. Twenty adult red flour beetles (*Tribolium castaneum*) were then placed into the dish and the dish was kept in a constant-temperature room at 25° C. 24 Hours later, the number of the dead insects was counted and % mortality was assessed. The tests were conducted with three replicates for a particular value of the concentration of the active compound under test, and the average of % mortality was calculated. The results (expressed as the averaged % mortality) are given in Table 3 below.

TABLE 3

| | Mortality (%) Concentration of active compound sprayed (ppm) | |
|---|---|---|
| Test Compounds | 300 | 100 |
| Compound No. 1 | 100 | 97 |
| Compound No. 2 | 100 | 100 |
| Compound No. 3 | 100 | 90 |
| Compound No. 4 | 100 | 97 |
| Compound No. 5 | 100 | 90 |
| Compound No. 6 | 100 | 90 |
| Compound No. 7 | 100 | 97 |
| Compound No. 8 | 100 | 90 |
| Compound No. 9 | 100 | 97 |
| Compound No. 10 | 100 | 90 |
| Compound No. 11 | 100 | 100 |
| Compound No. 12 | 100 | 100 |
| Compound No. 13 | 100 | 90 |
| Compound No. 14 | 100 | 97 |
| Compound No. 15 | 100 | 97 |
| Compound No. 16 | 100 | 97 |
| Compound No. 17 | 100 | 90 |
| Comparative compound A | 77 | 43 |
| Comparative compound B | 77 | 40 |
| Comparative compound C | 83 | 43 |
| Comparative compound D | 83 | 65 |
| Comparative compound E | 83 | 58 |
| Comparative compound F | 77 | 50 |
| Comparative compound G | 100 | 67 |
| Comparative compound H | 83 | 50 |
| No treatment (Control) | 0 | |

EXAMPLE 10

This Example illustrates the test of estimating the effect of the test compounds for controlling "resistant" strains of green rice leafhopper.

Aquatic rice plants of an average height of about 40 cm were planted in a pot of square cross-section (6 cm×6 cm) and made of black colored polyvinyl chloride. These aquatic rice plants were treated by dusting thereon the dusting powder of this invention made in the Example 6, at the rate of application of the active compound as indicated in Table 4 below. After the dusting treatment, the treated rice plants were covered with a cylindrical box of 11 cm diameter in the cross-section and made of polyvinyl chloride. Twenty adult female green rice leafhoppers (*Nephotettix cincticeps*) of 3 days old after the emergence of such "resistant" strain which showed the resistance against the known organophosphorus type insecticides and against the known carbamate-type insecticides were released into and confined in the cylindrical box containing the treated aquatic rice plants. The rice plants-cultivating pot, together with the covering cylindrical box of polyvinyl chloride, was kept in a constant-temperature room at 25° C. 48 Hours after the releasing of the insects, percent of the mortality was assessed. The tests were conducted with three replicates for a particular value of the concentration of the active compound under test, and the average of % mortality was calculated. The results (expressed as averaged % mortality) are set out in Table 4 below.

TABLE 4

| | Mortality (%) Rate of application of active compound (g/10 ares) | |
|---|---|---|
| Test Compounds | 15 | 5 |
| Compound No. 1 | 100 | 95 |
| Compound No. 2 | 100 | 100 |
| Compound No. 3 | 100 | 93 |
| Compound No. 4 | 100 | 95 |
| Compound No. 5 | 100 | 93 |
| Compound No. 6 | 100 | 93 |
| Compound No. 7 | 100 | 97 |
| Compound No. 8 | 100 | 93 |
| Compound No. 9 | 100 | 95 |
| Compound No. 10 | 100 | 93 |
| Compound No. 11 | 100 | 98 |
| Compound No. 12 | 100 | 98 |
| Compound No. 13 | 100 | 93 |
| Compound No. 14 | 100 | 95 |
| Compound No. 15 | 100 | 97 |
| Compound No. 16 | 100 | 97 |
| Compound No. 17 | 100 | 93 |
| Comparative Compound A | 73 | 37 |
| Comparative Compound B | 67 | 23 |
| Comparative Compound C | 67 | 37 |
| Comparative Compound D | 73 | 20 |
| Comparative Compound E | 90 | 47 |
| Comparative Compound F | 73 | 33 |
| Comparative Compound G | 93 | 50 |
| Comparative Compound H | 87 | 33 |
| No treatment (Control) | 0 | |

EXAMPLE 11

This Example illustrates the test of estimating the effect of test compounds for controlling green peach aphid.

Young seedlings of egg plant were cultivated in a pot of square cross-section (6 cm×6 cm), and these young egg plants were infested with 20 adult wingless green peach aphids (*Myzus persicae*) which had been reared over some successive generations. The infested egg plant was kept in a constant-temperature room for 24 hours. After the aphids on the egg plant started to reproduce, the egg plant with the infesting green peach aphids was sprayed with the composition under test which was prepared by diluting with water the emulsifiable concentrate of this invention made in the Example 4 to the concentration of the active compound as indicated in Table 5 below. The composition was applied at the rate of 30 ml per pot. The pot was subsequently kept in a constant-temperature room at 25° C. 5 Days after the spraying, the number of the green peach aphids which was infesting the egg plant was counted, and percent of mortality was calculated. The tests were conducted with three replicates for a particular value of the concentration of the active compound under test, and the average of % mortality was calculated.

The results (expressed as averaged % mortality) are given in Table 5 below.

TABLE 5

| Test Compounds | Mortality (%) Concentration of active compound sprayed (ppm) | |
| --- | --- | --- |
|  | 100 | 50 |
| Compound No. 1 | 100 | 90 |
| Compound No. 2 | 100 | 100 |
| Compound No. 3 | 100 | 90 |
| Compound No. 4 | 100 | 90 |
| Compound No. 5 | 100 | 90 |
| Compound No. 6 | 100 | 90 |
| Compound No. 7 | 100 | 90 |
| Compound No. 8 | 100 | 90 |
| Compound No. 9 | 100 | 90 |
| Compound No. 10 | 100 | 90 |
| Compound No. 11 | 100 | 98 |
| Compound No. 12 | 100 | 94 |
| Compound No. 13 | 100 | 90 |
| Compound No. 14 | 100 | 90 |
| Compound No. 15 | 100 | 90 |
| Compound No. 16 | 100 | 90 |
| Compound No. 17 | 100 | 90 |
| Comparative compound A | 84 | 59 |
| Comparative compound B | 85 | 40 |
| Comparative compound C | 88 | 57 |
| Comparative compound D | 85 | 51 |
| Comparative compound E | 93 | 45 |
| Comparative compound F | 92 | 57 |
| Comparative compound G | 100 | 63 |
| Comparative compound H | 94 | 57 |
| No treatment (Control) | 0 | |

EXAMPLE 12

This Example illustrates the test of controlling housefly.

A sheet of filter paper was placed on the bottom of a glass Petri dish of 9 cm diameter, and the filter paper was sprayed with 1 ml of a composition under test which was prepared by diluting with water the wettable powder of this invention made in the Example 5, to a concentration of the active compound as indicated in Table 6 below. 10 Adult houseflies (*Musca domestica*) of 4 days old after the emergence were released into and confined in the covered dish. The dish containing the houseflies was kept in a constant-temperature room at 25° C. 48 Hours later, the number of dead insects was counted and % mortality was assessed. The tests were conducted with three replicates for a particular value of the concentration of the active compound under test, and the average of % mortality was calculated. The results (expressed as the averaged % mortality) are set out in Table 6 below.

TABLE 6

| Test Compounds | Mortality (%) Concentration of active compound sprayed (ppm) | |
| --- | --- | --- |
|  | 300 | 100 |
| Compound No. 1 | 100 | 97 |
| Compound No. 2 | 100 | 100 |
| Compound No. 3 | 100 | 97 |
| Compound No. 4 | 100 | 93 |
| Compound No. 5 | 100 | 97 |
| Compound No. 6 | 100 | 97 |
| Compound No. 7 | 100 | 97 |
| Compound No. 8 | 100 | 93 |
| Compound No. 9 | 100 | 93 |
| Compound No. 10 | 100 | 97 |
| Compound No. 11 | 100 | 100 |
| Compound No. 12 | 100 | 100 |
| Compound No. 13 | 100 | 93 |
| Compound No. 14 | 100 | 97 |
| Compound No. 15 | 100 | 97 |
| Compound No. 16 | 100 | 97 |
| Compound No. 17 | 100 | 93 |
| Comparative compound A | 70 | 43 |
| Comparative compound B | 87 | 50 |
| Comparative compound C | 87 | 40 |
| Comparative compound D | 70 | 43 |
| Comparative compound E | 83 | 43 |
| Comparative compound F | 87 | 37 |
| Comparative compound G | 93 | 50 |
| Comparative compound H | 87 | 43 |
| No treatment (Control) | 0 | |

EXAMPLE 13

This Example illustrates the test of estimating the effect of the new compounds for controlling two-spotted spider mite.

Kidney-bean plants at the single true-leaf-extending stage planted in a pot of square cross-section (6 cm×6 cm) were infested with adult female two-spotted spider mites (*Tetranychus urticae*) which were reared over some successive generations. The number of the mites infested was 20 per pot. The infesting mites were allowed to produce the eggs on the bean plants. 24 Hours after the infestation, the bean plants and the mites were sprayed with 30 ml/pot of the composition under test which was prepared by diluting with water the wettable powder of this invention made in the Example 5 to a concentration of the active compound as indicated in Table 7 below. The treated plants in the pot were kept in a constant-temperature room at 25° C. 3 Days after the spraying, the numbers of dead mites and surviving mites were counted and the percent mortality was assessed in the same manner as in Example 10. The tests were conducted with three replicates for a particular value of the concentration of the active compound under test, and the average of mortality (%) was calculated. The results (expressed as the averaged % mortality) are given in Table 7 below.

TABLE 7

| Test Compounds | Mortality (%) Concentration of active compound sprayed (ppm) | |
|---|---|---|
| | 100 | 50 |
| Compound No. 1 | 100 | 95 |
| Compound No. 2 | 100 | 100 |
| Compound No. 3 | 100 | 95 |
| Compound No. 4 | 100 | 92 |
| Compound No. 5 | 100 | 99 |
| Compound No. 6 | 100 | 99 |
| Compound No. 7 | 100 | 93 |
| Compound No. 8 | 100 | 95 |
| Compound No. 9 | 100 | 95 |
| Compound No. 10 | 100 | 93 |
| Compound No. 11 | 100 | 100 |
| Compound No. 12 | 100 | 95 |
| Compound No. 13 | 100 | 95 |
| Compound No. 14 | 100 | 99 |
| Compound No. 15 | 100 | 99 |
| Compound No. 16 | 100 | 92 |
| Compound No. 17 | 100 | 99 |
| Comparative compound A | 75 | 25 |
| Comparative compound B | 85 | 38 |
| Comparative compound C | 87 | 50 |
| Comparative compound D | 82 | 44 |
| Comparative compound E | 63 | 44 |
| Comparative compound F | 85 | 53 |
| Comparative compound G | 87 | 63 |
| Comparative compound H | 78 | 37 |
| No treatment (Control) | 0 | |

EXAMPLE 14

This Example illustrates the test under submerged condition of estimating the effect of the test compounds for controlling small brown planthopper.

Aquatic rice plants were transplanted and cultivated under the submerged condition in a pot having an area of 1/10,000 ares at the soil surface. When the aquatic rice plants so cultivated reached a 4-leave stage, the granules of this invention prepared in the Example 7 were scattered onto the surface of the submerging water where the pot was immersed. The granules were applied at the rate of application of the active compound as indicated in Table 8 below. The test plots were classified into two, the first plot was such that two days lapsed between the application of the granules and the release of the insect pests under test; and the second plot was such that 5 days lapsed between the application of the granules and the release of the insect pests. The predetermined 2 or 5 days later, the pot was covered with a cylindrical box made of a plastic resin material and having 10 cm diameter and 30 cm height. Into the box covering the pot were released and confined therein 20 adult small brown planthoppers (*Laodelphax striattellus*). 48 Hours after the release of the planthoppers, the number of the dead insects was counted and % mortality was assessed. The tests were conducted with three replicates for a particular value of the concentration of the active compound under test, and the average of % mortality was calculated. The results (expressed as the averaged % mortality) are set out in Table 8 below.

TABLE 8

| Test Compounds | Mortality (%) Rate of application of active compound (g/10 ares) | | | |
|---|---|---|---|---|
| | 2 Days-lapsing plot | | 5 Days-lapsing plot | |
| | 200 | 50 | 200 | 50 |
| Compound No. 2 | 100 | 100 | 100 | 97 |
| Compound No. 7 | 100 | 90 | 97 | 90 |
| Compound No. 11 | 100 | 100 | 100 | 97 |
| Compound No. 12 | 100 | 100 | 100 | 93 |
| Compound No. 15 | 100 | 90 | 95 | 90 |
| Comparative compound B | 63 | 27 | 33 | 0 |
| Comparative compound F | 93 | 30 | 37 | 10 |
| Comparative compound G | 100 | 43 | 43 | 17 |
| No treatment (Control) | 0 | | 0 | |

EXAMPLE 15

This Example illustrates the test of estimating the effect of test compounds for controlling southern root-knot nematode.

A quantity of soil infested by southern root-knot nematode (*Meloidogyne incognita*) was admixed with a predetermined amount of the granules of this invention prepared in the Example 7 to such concentration of the active compound as indicated in Table 9. The mixture of the soil and the granules was stirred and mixed uniformly and then charged into a pot having an area of 1/5,000 ares. In the treated soil charged in the pot were sown 20 seeds of tomato plant per pot. The tomato seeds were cultivated in a greenhouse. 4 Weeks after the seed sowing, the grown roots of the young tomato plant were withdrawn from the soil without damaging the roots, and the degree of injury of the roots was evaluated according to the following ratings to estimate the root-knot index:

Ratings of root-knot (Degree of injury):

0—No root-knot formation (perfect control).
1—Slight root-knot formation was observed at the tip of small side-roots.
2—Root-knot formation was observed in the small side-roots but the knots formed were not yet connected with each other.
3—Root-knot formation was observed along the whole length of the small side-roots with some knots being connected with each other.
4—Root-knot formation was observed in the main root, too, with the many knots in the side-roots being connected with each other.
5—The number of root-knots formed were very much great, with the knots connected with each other in the main root and also in the side-roots (corresponding to the "control" plot where no treatment was made).

Root-knot index was estimated according to the following equation:

$$\text{Root-knot index}(\%) = \frac{\Sigma \text{ (Rating value} \times \text{Number of roots alloted the same rating value)}}{\text{(Total number of plants under test)} \times 5} \times 100$$

The tests were conducted with three replicates for a particular value of the concentration of the active compound under test, and the average of the estimated root-knot indexes was calculated. The results (expressed as the averaged % root-knot index) are listed in Table 9 below.

TABLE 9

| Test Compound | Root-knot Index (%) Rate of application of active compound (Kg/10 ares) | |
|---|---|---|
| | 3 | 1 |
| Compound No. 2 | 0 | 8 |
| Compound No. 7 | 0 | 14 |
| Compound No. 11 | 0 | 11 |
| Compound No. 12 | 0 | 14 |
| Compound No. 15 | 2 | 21 |
| Comparative compound B | 27 | 78 |
| Comparative compound F | 20 | 62 |
| Comparative compound G | 12 | 63 |
| No treatment (Control) | | 98 |

EXAMPLE 16

This Example illustrates the test of estimating the insecticidal activity of test compounds against Thrips palmi.

A piece of the foliage of musk-melon which was cut off by means of a leaf-punch of 8 cm diameter was immersed for 10 seconds in a volume of the composition under test which was prepared by diluting with water the wettable powder of this invention made in the Example 5 to the concentration of the active compound indicated in Table 10 below. The foliage piece was dried in air and then placed on the bottom of a Petri dish of 9 cm diameter. Ten adult Thrips palmi were subsequently placed and confined in said dish, and the dish was kept in a constant-temperature room at 25° C. 48 Hours later, the number of the dead insects was counted and % mortality was assessed. The tests were conducted with three replicates for a particular value of the concentration of the active compound under test, and the average of % mortality was calculated. The test results are shown in Table 10 below.

TABLE 10

| Test Compounds | Mortality (%) Concentration of active compound used for treatment (ppm) | |
|---|---|---|
| | 500 | 100 |
| Compound No. 1 | 100 | 93 |
| Compound No. 2 | 100 | 100 |
| Compound No. 3 | 100 | 97 |
| Compound No. 4 | 100 | 87 |
| Compound No. 5 | 100 | 90 |
| Compound No. 6 | 100 | 90 |
| Compound No. 7 | 100 | 80 |
| Compound No. 8 | 100 | 83 |
| Compound No. 9 | 100 | 90 |
| Compound No. 10 | 100 | 100 |
| Compound No. 11 | 100 | 100 |
| Compound No. 12 | 100 | 83 |
| Compound No. 13 | 100 | 80 |
| Compound No. 14 | 100 | 100 |
| Compound No. 15 | 100 | 93 |
| Compound No. 16 | 100 | 100 |
| Compound No. 17 | 100 | 97 |
| Comparative compound A | 63 | 17 |
| Comparative compound B | 37 | 0 |
| Comparative compound C | 77 | 33 |
| Comparative compound D | 80 | 30 |
| Comparative compound E | 90 | 47 |
| Comparative compound F | 87 | 50 |
| Comparative compound G | 20 | 0 |
| Comparative compound H | 67 | 0 |
| No treatment (Control) | 0 | |

EXAMPLE 17

This Example illustrates the test of estimating the insecticidal activity of test compounds against comstock mealybug. A piece of pumpkin to which second-instar larvae of comstock mealybug (*Pseudococcus comstocki*) were infesting was immersed for 10 seconds in a volume of the composition under test which was prepared by diluting with water the wettable powder of this invention made in the Example 5 to the concentration of the active compound indicated in Table 11 below. After this treatment, the pumpkin piece with the insects was placed on a sheet of filter paper covering the bottom of a Petri dish of 9 cm diameter. The insects were confined in said dish, and the dish was kept in a constant-temperature room at 25° C. 48 Hours later, the number of the dead insects was counted under microscope, and % mortality was assessed. The tests were conducted with three replicates for a particular value of the concentration of the active compound under test, and the average of % mortality was calculated. The test results are shown in Table 11 below.

TABLE 11

| Test Compounds | Mortality (%) Concentration of active compound used for treatment (ppm) | |
|---|---|---|
| | 100 | 30 |
| Compound No. 1 | 100 | 96 |
| Compound No. 2 | 100 | 100 |
| Compound No. 3 | 100 | 90 |
| Compound No. 4 | 100 | 92 |
| Compound No. 5 | 100 | 97 |
| Compound No. 6 | 100 | 97 |
| Compound No. 7 | 100 | 95 |
| Compound No. 8 | 100 | 100 |
| Compound No. 9 | 100 | 94 |
| Compound No. 10 | 100 | 96 |
| Compound No. 11 | 100 | 91 |
| Compound No. 12 | 100 | 93 |
| Compound No. 13 | 100 | 90 |
| Compound No. 14 | 100 | 100 |
| Compound No. 15 | 100 | 98 |
| Compound No. 16 | 100 | 94 |
| Compound No. 17 | 100 | 96 |

TABLE 11-continued

| Test Compounds | Mortality (%) Concentration of active compound used for treatment (ppm) | |
|---|---|---|
| | 100 | 30 |
| Comparative compound A | 80 | 46 |
| Comparative compound B | 83 | 47 |
| Comparative compound C | 85 | 51 |
| Comparative compound D | 77 | 26 |
| Comparative compound E | 92 | 63 |
| Comparative compound F | 90 | 44 |
| Comparative compound G | 81 | 40 |
| Comparative compound H | 76 | 35 |
| No treatment (Control) | 0 | |

EXAMPLE 18

This Example illustrates the test of estimating the insecticidal activity of test compounds against twenty-eight-spotted ladybird.

A piece of the foliage of egg-plant which was cut off by means of a leaf-punch of 8 cm diameter was immersed for 10 seconds in a volume of the composition under test which was prepared by diluting with water the wettable powder of this invention made in the Example 5 to the concentration of the active compound indicated in Table 12 below. The foliage piece qas dried in air and then placed on the bottom of a Petri dish of 9 cm diameter. Ten larvae of twenty-eight-spotted ladybird (*Henosepilachna vigintioctopunctata*) were subsequently placed and confined in said dish, and the dish was kept in a constant-temperature room at 25° C. 48 Hours later, the number of the dead insects was counted and % mortality was assessed. The tests were conducted with three replicates for a particular value of the concentration of the active compound under test, and the average of % mortality was calculated. The test results are shown in Table 12 below.

TABLE 12

| Test Compounds | Mortality (%) Concentration of active compound used for treatment (ppm) | |
|---|---|---|
| | 300 | 100 |
| Compound No. 1 | 100 | 93 |
| Compound No. 2 | 100 | 100 |
| Compound No. 3 | 100 | 47 |
| Compound No. 4 | 100 | 100 |
| Compound No. 5 | 100 | 90 |
| Compound No. 6 | 100 | 97 |
| Compound No. 7 | 100 | 93 |
| Compound No. 8 | 100 | 100 |
| Compound No. 9 | 100 | 93 |
| Compound No. 10 | 100 | 100 |
| Compound No. 11 | 100 | 90 |
| Compound No. 12 | 100 | 93 |
| Compound No. 13 | 100 | 97 |
| Compound No. 14 | 100 | 100 |
| Compound No. 15 | 100 | 97 |
| Compound No. 16 | 100 | 100 |
| Compound No. 17 | 100 | 93 |
| Comparative compound A | 90 | 37 |
| Comparative compound B | 43 | 57 |
| Comparative compound C | 87 | 43 |
| Comparative compound D | 100 | 60 |
| Comparative compound E | 87 | 47 |
| Comparative compound F | 93 | 53 |
| Comparative compound G | 93 | 50 |
| No treatment (Control) | 0 | |

What we claim is:

1. A method of combating insect pests, acarine pests and/or nematode pests at a locus of infestation, which comprises treating the pests or the locus of infestation with an insecticidally, miticidally and/or nematocidally effective amount of a compound of the general formula:

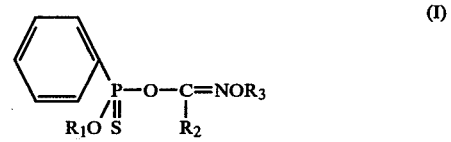

(I)

wherein $R_1$ denotes a lower alkyl group; $R_2$ denotes a hydrogen atom, a lower alkyl group or an unsaturated lower alkyl group; and $R_3$ denotes a lower alkyl group or an unsaturated lower alkyl group.

2. A pesticidal composition comprising as an active ingredient an insecticidally, miticidally and/or nematocidally effective amount of a compound of the general formula:

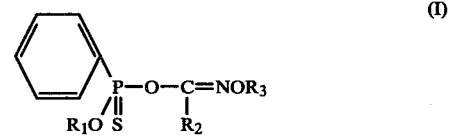

(I)

wherein $R_1$ denotes a lower alkyl group; $R_2$ denotes a hydrogen atom, a lower alkyl group or an unsaturated lower alkyl group and $R_3$ denotes a lower alkyl group or an unsaturated lower alkyl group in combination with an acceptable carrier or diluent.

3. Compounds of the general formula:

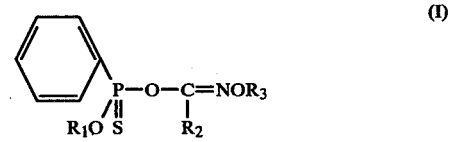

(I)

wherein $R_1$ denotes a lower alkyl group; $R_2$ denotes a hydrogen atom, a lower alkyl group or an unsaturated lower alkyl group; and $R_3$ denotes a lower alkyl group or an unsaturated lower alkyl group.

4. Compounds of the general formula:

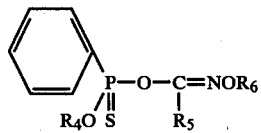

(I')

wherein $R_4$ is an alkyl group containing 1–6 carbon atoms, $R_5$ is a hydrogen atom, an alkyl group containing 1–6 carbon atoms, an alkenyl group containing 2–6 carbon atoms or an alkynyl group containing 2–6 carbon atoms, and $R_6$ is an alkyl group containing 1–6 carbon atoms, an alkenyl group containing 2–6 carbon atoms or an alkynyl group containing 2–6 carbon atoms.

5. Compounds according to claim 4 wherein $R_4$ is methyl or ethyl group; $R_5$ is hydrogen, methyl, ethyl, n-propyl, i-propyl, n-butyl, vinyl, propenyl or ethynyl group; and $R_6$ is methyl, ethyl, i-propyl, vinyl, allyl or propargyl group.

6. Compounds of the general formula:

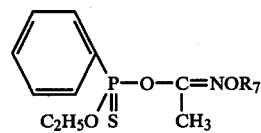

(I")

wherein $R_7$ is an alkyl group of 1–4 carbon atoms, an alkenyl group of 2–4 carbon atoms or an alkynyl group of 2–4 carbon atoms.

7. Compounds according to claim 6 wherein $R_7$ is methyl, ethyl, i-propyl, allyl or propargyl group.

8. A compound according to claim 3 selected from:

O-ethyl, O-(N-methoxyformimidoyl)phenylthionophosphonate;
O-ethyl, O-(N-methoxyacetimidoyl)phenylthionophosphonate;
O-ethyl, O-(N-methoxypropionimidoyl)phenylthionophosphonate;
O-ethyl, O-(N-methoxy-n-butyrimidoyl)phenylthionophosphonate;
O-ethyl, O-(N-ethoxy-i-butyrimidoyl)phenylthionophosphonate;
O-ethyl, O-(N-methoxyvalerimidoyl)phenylthionophosphonate;
O-ethyl, O-(N-methoxyacrylimidoyl)phenylthionophosphonate;
O-ethyl, O-(N-methoxycrotonimidoyl)phenylthionophosphonate;
O-ethyl, O-(N-ethoxypropionimidoyl)phenylthionophosphonate;
O-ethyl, O-(N-ethoxyacetimidoyl)phenylthionophosphonate;
O-ethyl, O-(N-i-propoxyacetimidoyl)phenylthionophosphonate;
O-ethyl, O-(N-allyloxyacetimidoyl)phenylthionophosphonate;
O-ethyl, O-(N-propargyloxyacetimidoyl)phenylthionophosphonate;
O-methyl, O-(N-methoxyacetimidoyl)phenylthionophosphonate;
O-methyl, O-(N-ethoxycrotonimidoyl)phenylthionophosphonate;
O-methyl, O-(N-i-propoxyacetimidoyl)phenylthionophosphonate; and
O-metyl, O-(N-allyloxyacetimidoyl)phenylthionophosphonate.

* * * * *